United States Patent [19]
Genna et al.

[11] Patent Number: 4,584,478
[45] Date of Patent: Apr. 22, 1986

[54] RADIONUCLIDE ANNULAR SINGLE CRYSTAL SCINTILLATOR CAMERA WITH ROTATING COLLIMATOR

[75] Inventors: Sebastian Genna; Sing-Chin Pang, both of Belmont, Mass.

[73] Assignee: Digital Scintigraphics, Inc., Belmont, Mass.

[21] Appl. No.: 470,475

[22] Filed: Feb. 28, 1983

[51] Int. Cl.$^4$ ............................................. G01T 1/20
[52] U.S. Cl. ............................................. 250/363 S
[58] Field of Search ...................... 250/363 S, 505.1

[56] References Cited

U.S. PATENT DOCUMENTS

| 4,095,107 | 6/1978 | Genna et al. | 250/363 S |
| 4,250,392 | 2/1981 | Leosk et al. | 250/363 S |
| 4,295,047 | 10/1981 | Koga et al. | 250/363 S |
| 4,389,569 | 6/1983 | Hattori et al. | 250/363 S |

FOREIGN PATENT DOCUMENTS

152261  6/1975  U.S.S.R. ........................ 250/363 S

Primary Examiner—Bruce C. Anderson
Assistant Examiner—Richard Hanig
Attorney, Agent, or Firm—Joseph S. Iandiorio; William E. Noonan

[57] ABSTRACT

A radionuclide emission tomography camera for sensing gamma ray emissions from a source within the field of view, including: a fixed position-sensitive detector, responsive to the gamma ray emissions and surrounding the field of view, for detecting the contact position and the trajectory from which a gamma ray emission originates; a rotatable collimator disposed between the fixed position-sensitive detector and the field of view and including at least one array of collimator elements for restricting and collimating the gamma ray emissions; and means for rotating the collimator relative to the fixed position-sensitive detector for exposing different sections of the position-sensitive detector to the gamma ray emissions in order to view the source from different angles.

2 Claims, 16 Drawing Figures

RADIONUCLIDE ANNULAR SINGLE CRYSTAL SCINTILLATOR CAMERA WITH ROTATING COLLIMATOR

FIELD OF INVENTION

This invention relates to a radionuclide annular single crystal scintillator camera with rotating collimator for both single photon emission tomography (SPECT) and multiple-view two-dimensional imagery.

BACKGROUND OF INVENTION

In typical two-dimensional emission imaging applications, a source of penetrating radiation is administered to the patient. Typically, this consists of a radiopharmaceutical capable of gamma ray emission. So-called "scintillation cameras" are capable of imaging an entire organ, such as the brain, without detector motion. In such cameras, a set of parallel lead collimated holes defines a set of columnar trajectories generally perpendicular to the camera face. The detector is constructed to be position sensitive, i.e., the trajectory from whence a gamma ray originated is identified. This permits direct construction of a two-dimensional projected image by an intensity format on a cathode ray tube and a hard copy such as film.

While two-dimensional radionuclide emission techniques are widely used, it has been recognized that they suffer from significant drawbacks. Thus, a three-dimensional radionuclide distribution in the interior of an object under examination appears with its details from front to back superimposed. Consequently, the resulting two-dimensional image is often difficult to interpret in that concentrations of activity within small volumes are often not identifiable or adequately pinpointed.

Techniques for three-dimensional image reconstruction of the distribution of gamma-emitting radionuclides have also been developed. These techniques, which are usually referred to as "single photo-emission computed tomography" (SPECT), require a large number, e.g. 60 to 120, of two-dimensional images to be recorded from different angles-of-view encircling the source object. When scintillation cameras are used to obtain these images a camera having a planar detector is conventionally employed. It is positioned with its planar crystal surface parallel to an axis of rotation through the source object. Separate images are obtained with the camera rotated sequentially by $\Gamma\theta$ until an entire sequence of images (through 360 degrees) encircling the object is obtained. This set of two-dimensional images contains the data necessary for three-dimensional transaxial image reconstruction by conventional means, as disclosed in U.S. Pat. No. 4,095,107.

Typically, such devices have limited sensitivity because the gamma rays are detected only in one direction, one view at a time. The sensitivity may be increased by adding a second camera, but further sensitivity cannot be increased in this manner since two is about the upper limit on the number of cameras because they are bulky and would not readily fit together. The cameras are heavy because of the lead shielding. Their weight is on the order of thousands of pounds. Mechanical rotation of them is therefore difficult and costly. The rotation of these cameras necessarily results in some measure of misalignment, which will degrade the image. Alignment is made more difficult by the great weight and size of the cameras. Further, image non-uniformity errors reinforce upon reconstruction of the three-dimensional images because irregularities and non-linearities in position analysis in each view are in phase with each other since each view has the same error of profile. In addition, due to the motion of the camera, the accuracy of the imaging process is distorted because of the changing orientation of the camera with respect to the environmental magnetic field, such as the earth's magnetic field.

SUMMARY OF INVENTION

It is therefore an object of this invention to provide an improved radionuclide camera in which there is no need for motion of the heavy camera detector.

It is a further object of this invention to provide an improved radionuclide camera in which motion is required of only the relatively lightweight collimator.

It is a further object of this invention to provide an improved radionuclide camera in which accurate alignment about the center of rotation is more easily achieved.

It is a further object of this invention to provide an improved radionuclide camera in which sensitivity can be increased fourfold relative to planar cameras.

It is a further object of this invention to provide an improved radionuclide camera in which non-uniformities are dampened on reconstruction of three-dimensional images because irregularities and non-linearities in position analysis are not in phase.

It is a further object of this invention to provide an improved radionuclide camera in which the deleterious effect of the environmental magnetic field on the camera imaging process can be eliminated because the orientation of the camera to the field is constant.

It is a further object of this invention to provide an improved radionuclide camera in which multiple two-dimensional images can be recorded at the same time using the same detector system and electronic hardware.

This invention features a radionuclide emission tomography camera for sensing gamma ray emissions from a source within the field of view. There is a fixed position-sensitive detector means responsive to the gamma ray emissions and surrounding the field of view for detecting the contact position and the form which a gamma ray emission originates. Rotatable collimator means situated between the fixed position-sensitive detector means and the field of view includes at least one array of collimator elements for restricting and collimating the gamma ray emissions. There are means for rotating the collimator means relative to the fixed position-sensitive detector for exposing different sections of the position-sensitive detector to the gamma ray emissions in order to view the source from different angles.

In a preferred embodiment, the collimator means includes a plurality of arrays of collimator elements. The elements may be parallel, they may converge in a plane normal to the axis of rotation, or they may diverge in a plane normal to the axis of rotation. The collimator elements may also diverge or converge in a plane containing the axis of rotation. The fixed position-sensitive detector may include a scintillation means and a photosensor means. The scintillation means may include a single continuous stationary scintillation crystal. Typically, the collimator means is annular and the scintillation means and the photosensor means are annular also.

DISCLOSURE OF PREFERRED EMBODIMENT

Other objects, features and advantages will occur from the following description of a preferred embodiment and the accompanying drawings, in which.

Figure 1:
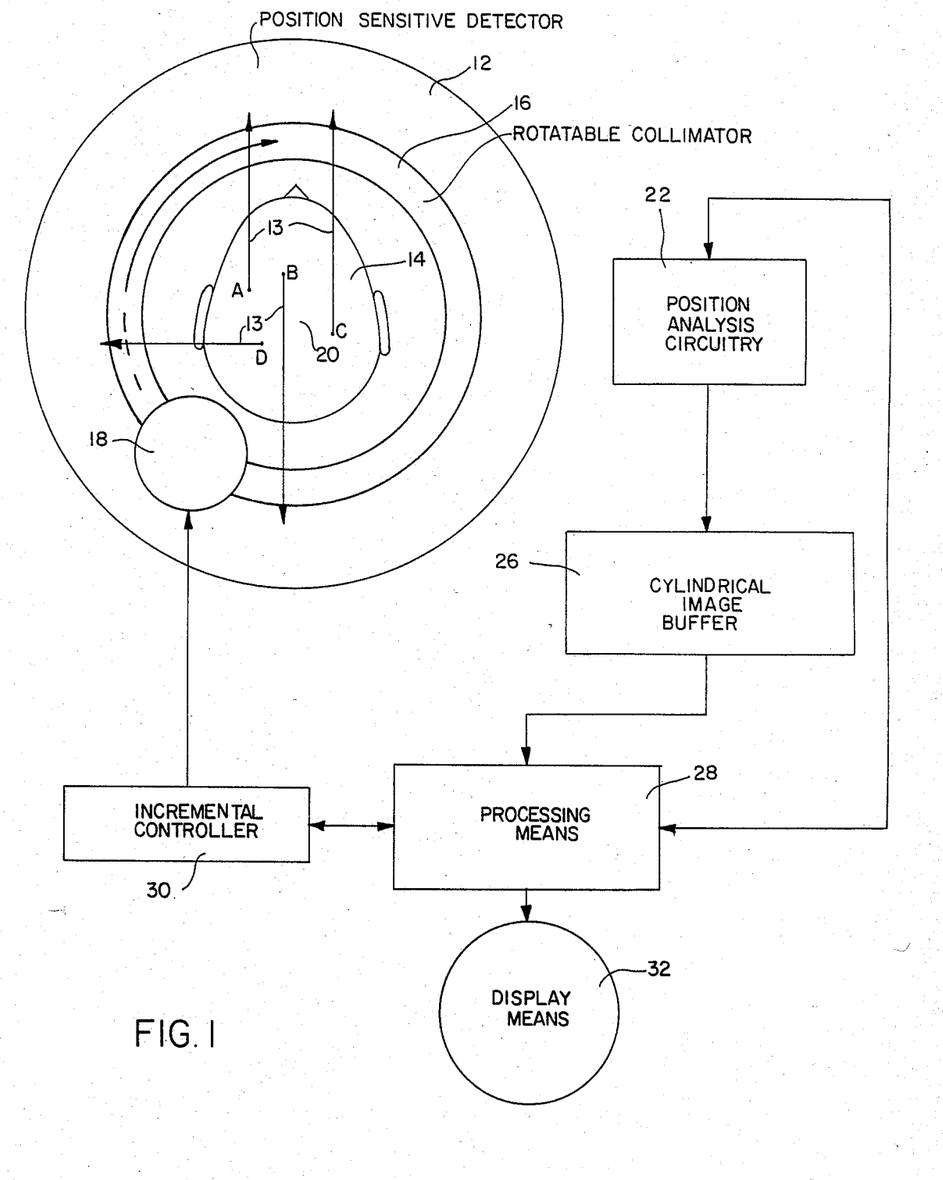
FIG. 1 is a block diagram of a radionuclide camera according to this invention including certain portions of the associated information processing system.

There is shown in FIG. 1 a simplified block diagram of a cylindrical radionuclide emission tomography camera 10 with a stationary position-sensitive detector 12 and rotatable collimator 16 according to this invention. Object 14, typically a human body part, is positioned within the field of view of the radionuclide camera 10. Position-sensitive detector means 12 receives and is sensitive to gamma rays 13 impinging thereupon from radiopharmaceutical concentrations A, B, C, and D contained in object 14 within the field of view. Collimator 16 contains an array of parallel collimator tubes or elements which together with additional lead shielding comprise a continuous ring surrounding the field of view and through which gamma rays may pass only via the tubular collimator elements.

Collimator 16 is rotatable by rotation means 18 about cylindrical rotation (Z) axis 20 and can be specifically positioned to restrict gamma ray penetration to certain areas of position-sensitive detector means 12 by rotating the array of tubular collimator elements to specific angles $\theta$. In this position the lead material of collimator 16 prevents all gamma ray penetration except that which is aligned with the tubular collimator elements. Rotation of collimator 16 about the rotation axis 20 effects the relative orientation of the two-dimensional exposure viewed by the camera. Sequential rotation of collimator 16 incrementally through 360 around the field of view enables the accumulation of the entire series of two-dimensional images necessary for three-dimensional image reconstruction.

The output from position-sensitive detector means 12 is delivered to position analysis circuit 22, such as the device disclosed in applicants' U.S. Pat. No. 4,228,515, which determines the actual position ($\theta$, Z) of each scintillation event within the position-sensitive detector means 12, caused by gamma ray emission 13 from concentrations such as A, B, C or D. Position analysis circuit 22 calculates the position of a scintillation event and directs the specific address of the image buffer means 26 corresponding to the calculated position to be incremented by one. The procedure repeats for each of a large number of scintillation events, e.g. 10,000–100,000, for a preset time monitored by the processing means 28, at which time the image buffer contains a two-dimensional numerical image representation of the radioactive source distribution. Processing means 28 monitors rotation means 18 to determine the position of collimator 16 and signals incremental controller 30, causing rotation means 18 to step collimator 16 to the next sequential incremental position. Processing means 28 also fetches data from and clears cylindrical image buffer 26. This enables the accumulation of the next set of exposure data in the series. Processing means 28 produces a three-dimensional image representation of the radioactive source distribution within the object within the field of view by transaxial image reconstruction from the entire series of incremental exposure image data delivered by image buffer means 26 from each incremental viewing position. This is accomplished by traditional reconstruction techniques such as those disclosed in U.S. Pat. No. 4,095,107. Transaxial reconstruction from the series of two-dimensional images results in the three-dimensional image of the source distribution, which may be displayed by means of display means 32.

Figure 2:
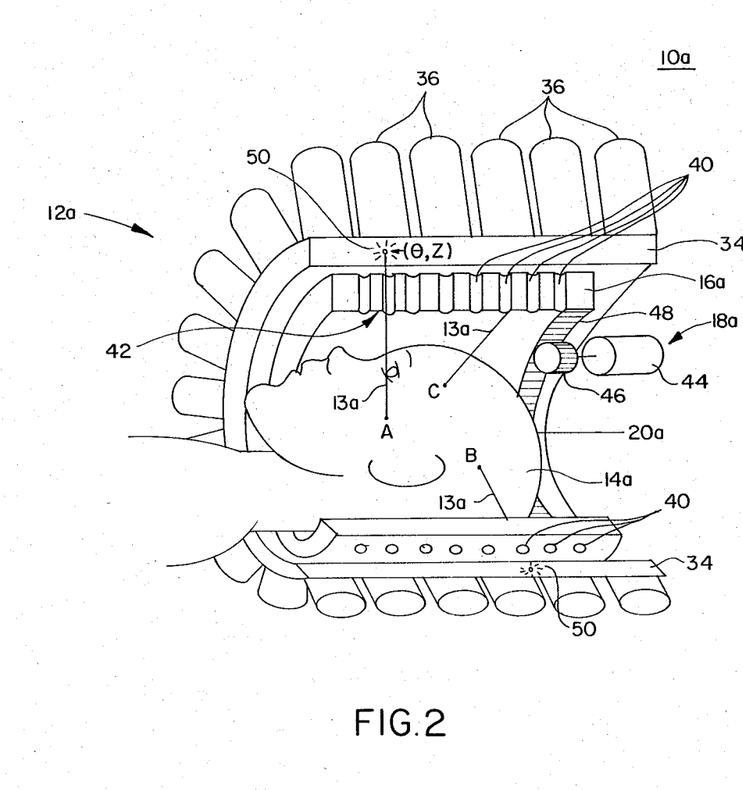
FIG. 2 is an enlarged view of a portion of the camera showing the detector and rotatable collimator.

Position-sensitive detector means 12a in camera 10a, FIG. 2, may include a single stationary scintillation crystal 34 and a plurality of stationary photomultipliers 36. Collimator 16a is comprised of a lead shielding material and includes at least one array 42 of tubular collimator elements 40. Collimator 16a is rotatable in its position between the object 14a and the scintillation crystal 34, thereby restricting the passage of gamma rays 13a from radionuclide disintegration within object 14a. Only those gamma ray emissions 13a from A and B aligned with tubular collimator elements 40, penetrate collimator 16a and impinge upon scintillation crystal 34. The remaining gamma rays 13a such as from point C are blocked by the lead shielding material of collimator 16a. This enables the gamma ray emissions to yield a separate two-dimensional exposure for each orientation relative to the field of view as rotatable collimator 16a is stepped through 360 degrees by rotation means 18a, which may include a motor 44 and drive gear 46, which meshes with a ring gear 48 on collimator 16a.

The series of photomultipliers 36 positioned behind scintillation crystal 34 are able to detect light photons from scintillations 50 occurring within scintillation crystal 34. The pulse signals from photomultipliers 36 as a result of a scintillation 50 are used by the position analysis circuit 22, FIG. 1, to determine the position ($\theta$, Z) of a scintillation event, as disclosed in U.S. Pat. No. 4,228,515.

In order to accumulate the necessary series of sequential exposures, collimator 16 is incrementally rotated by rotation means 18a about the Z axis of rotation 20a of object 14. This enables the gamma ray emissions 13a such as from points A and B to pass through tubular collimator elements 40 and impinge upon associated portions of the scintillator crystal 34 at various angles of view completely encircling the source distribution through the 360 degrees. The resulting series of sequential exposures is processed as described in FIG. 1.

Figure 3A:
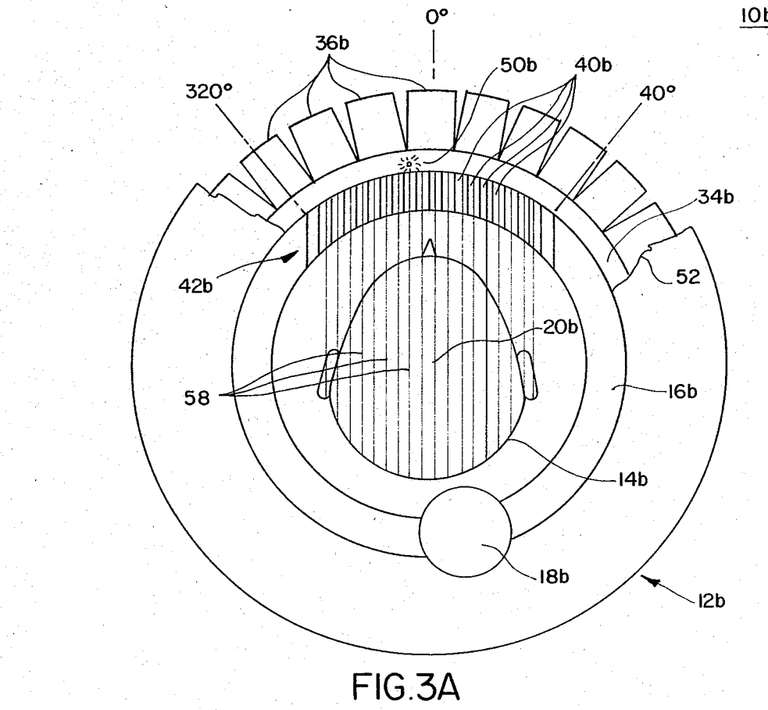
FIG. 3A is an end view of a radionuclide camera according to this invention having a collimator with a single array of collimator elements.
Figure 3B:
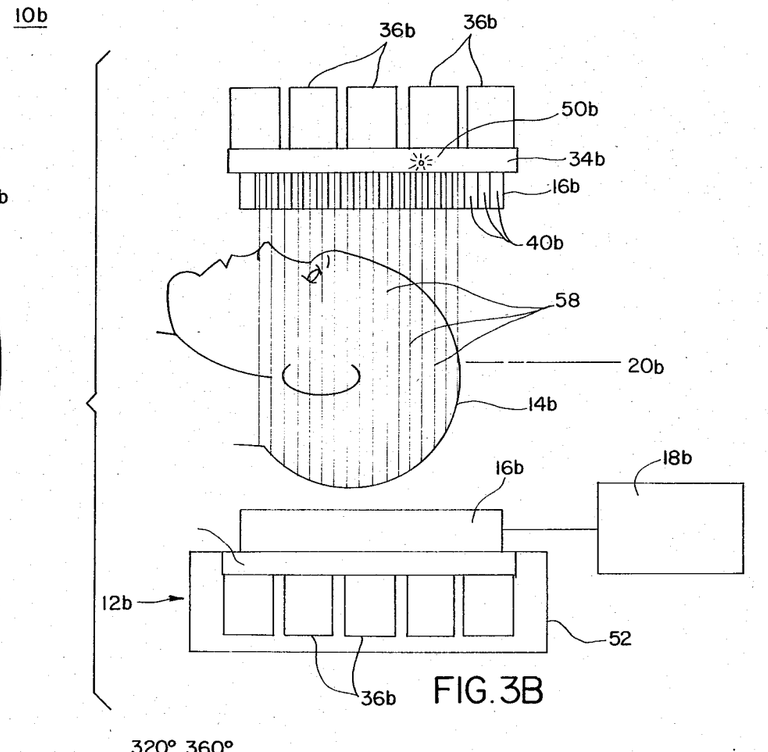
FIG. 3B is a side sectional view of FIG. 3A.
Figure 3C:
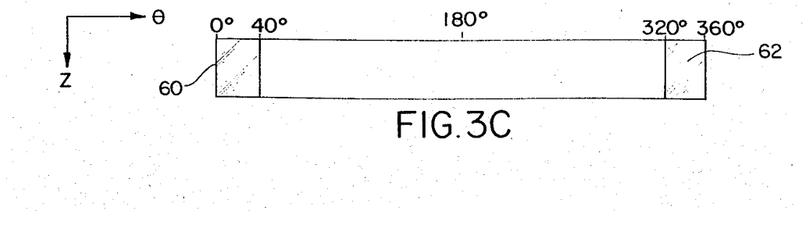
FIG. 3C is an illustration showing the $\theta,Z$ image field corresponding to the annular arc of the scintillation crystal.

Camera 10b, having collimator 16b with but a single array 42b of collimator elements 40b, is shown in FIG. 3A with lead shield 52 in place around photomultipliers 36b. The angle of scintillation crystal 34b subtended by array 42b is approximately 80 degrees and extends 40 degrees on either side of the $\theta_0$ position, from 320 degrees on the left to 40 degrees on the right. As shown in FIG. 3B, scintillation crystal 34b is continuous in the cylindrical direction and also for a substantial distance along the Z axis, or rotation axis, 20b. The angle subtended by array 42b on scintillation crystal 34b is shown in graphical form in FIG. 3C, where the $\theta_0$ position at zero and 360 is shown at either end and the shaded portions 60, 62, each of 40 degrees, are shown at the left and right ends. All of the gamma rays which follow the paths 58 in the two dimensions shown in FIGS. 3A and 3B create the two-dimensional image on areas 60 and 62 of the image field of the scintillation crystal 34b.

Figure 4A:
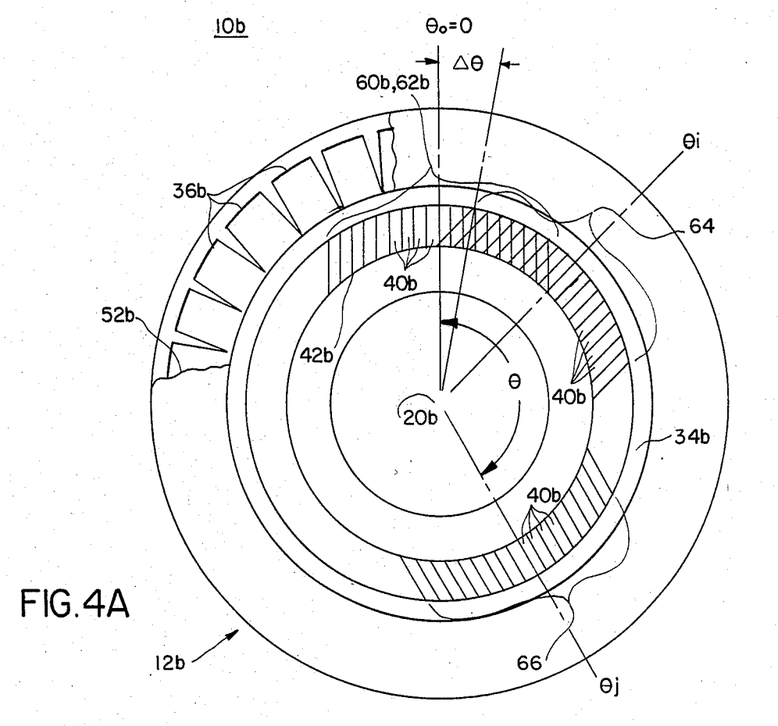
FIG. 4A is an end view of the camera similar to FIG. 3A showing the collimator in three different rotated positions.
Figure 4B:
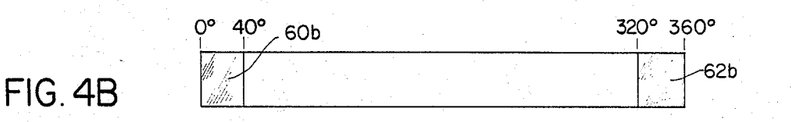
FIGS. 4B, 4C and 4D are illustrations of the image fields of the areas of the scintillation crystal associated with each of the three positions depicted in FIG. 4A.
Figure 4C:
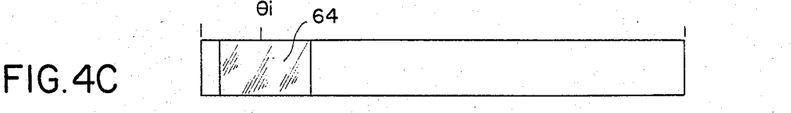
Figure 4D:
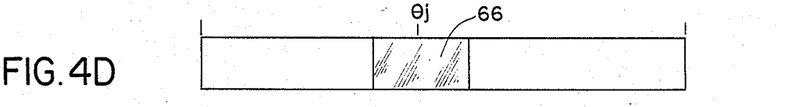

By rotating collimator 16b, as shown in FIGS. 4A-D, a number of views may be obtained, for example, the view centered at $\theta_0$, FIG. 4A; the view centered at $\theta_i$; and the view centered at $\theta_j$. The first view, at $\theta_0$, provides the image area on scintillation crystal 34b having the two abutting areas, areas 60b and 62b, as shown in FIG. 4B. At position $\theta_i$, the area on scintillation crystal 34b is represented by area 64, and at the position $\theta_j$ the area on scintillation crystal 34b is represented by area 66.

Figure 5A:
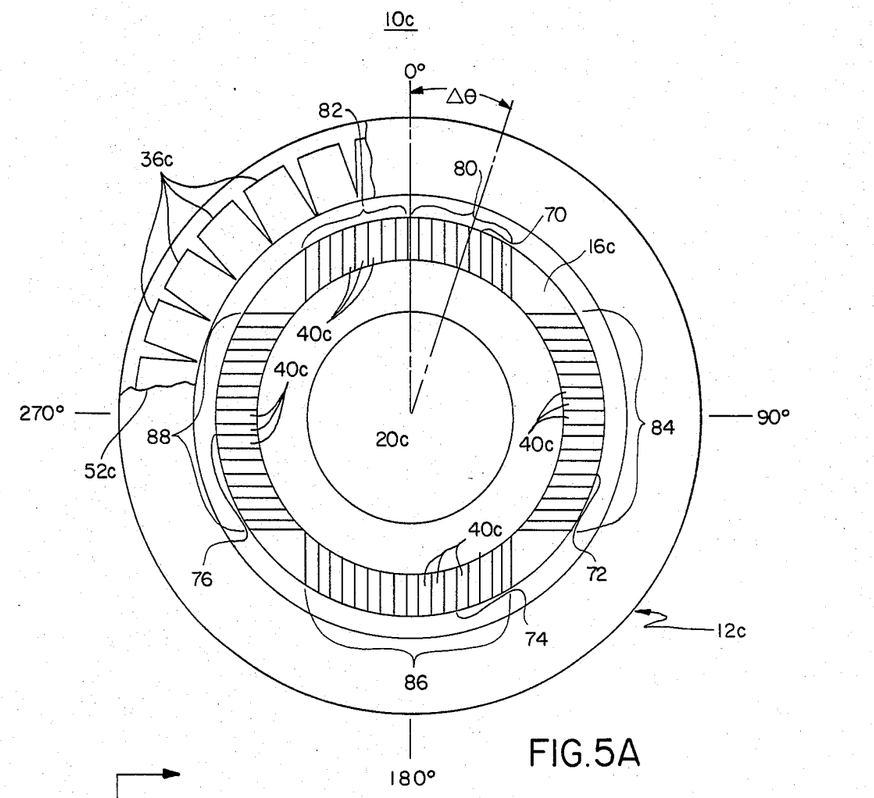
FIG. 5A is an end view of a radionulclide camera according to this invention having four separate arrays of collimator elements.
Figure 5B:
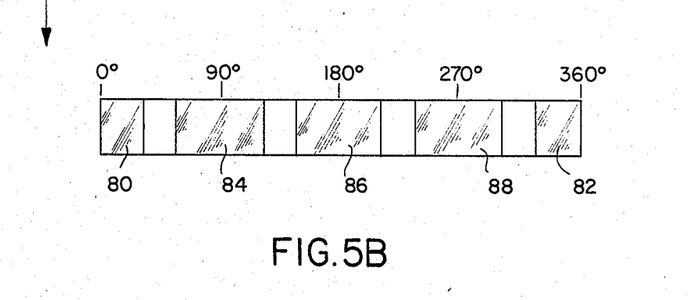
FIG. 5B is an illustration of the image fields of the areas of the scintillation crystals corresponding to the four arrays of FIG. 5A.

Although thus far the camera has been shown with but a single array, that is not a necessary limitation of the invention, for as shown in FIGS. 5A and 5B, camera 10c may include a collimator 16c which has a number of arrays, for example four arrays 70, 72, 74, 76, each formed from a plurality of tubular holes 40c. With such a construction, each of the four arrays 70, 72, 74 and 76 corresponds to a different area on the scintillation crystal 34c. For example, array 70 corresponds to areas 80 and 82, FIG. 5B; array 72 corresponds to area 84; array 74 corresponds to area 86; and array 76 corresponds to area 88. Subsequently, as collimator 16c is rotated, each of the arrays 70, 72, 74 and 76 will provide additional areas of exposure on scintillation crystal 34c so that a number of views of different areas will be obtained until all the preselected angles are viewed. For example, the entire rotation may be from zero to 90 degrees so that each of the arrays finally takes the original position of the next successive clockwise array. The steps may be very small, e.g. one or two degrees, or may be in steps of ten to fifteen degrees, depending upon the number of views that are desired for the information processing.

Figure 6A:
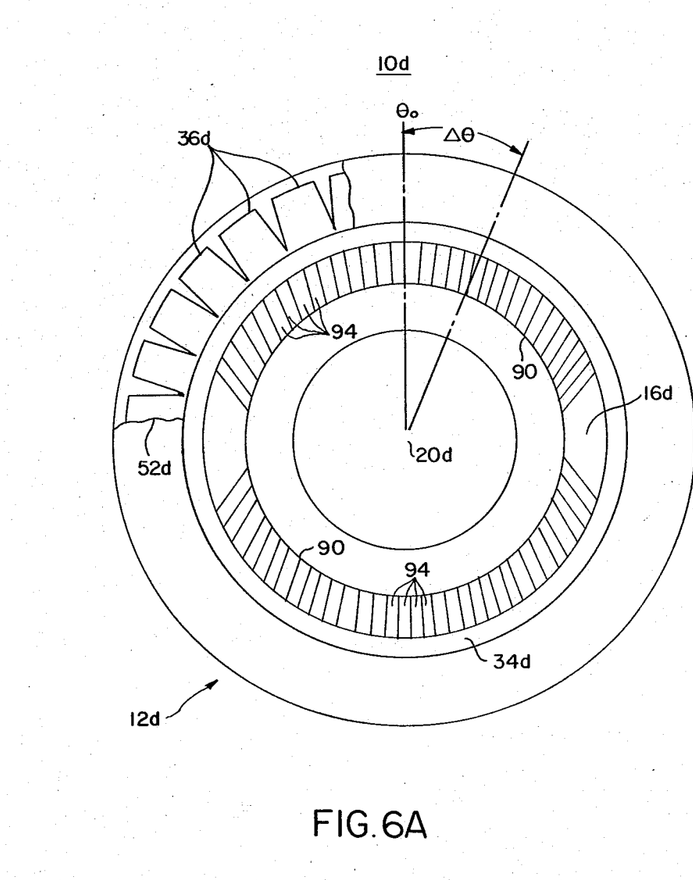
FIG. 6A is an end view of the camera according to this invention having a collimator with converging collimator elements.
Figure 6B:
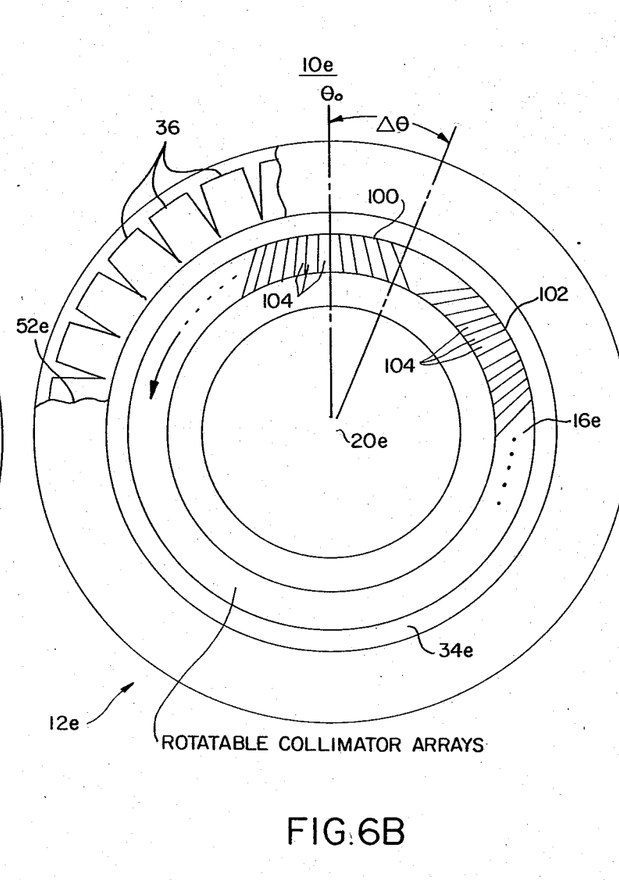
FIG. 6B is a view similar to FIG. 6A having a collimator with diverging collimator elements.

Although thus far the collimators have been shown with the tubular collimator elements parallel to each other, this is not a necessary limitation of the invention. For example, as shown in FIG. 6A, camera 10d may include collimator 16d having two arrays 90, 92, each of which is composed of tubular collimator elements 94 which are converging toward the Z axis or rotational axis 20d when viewed in a plane normal to the rotational axis 20d. Alternatively, as shown in FIG. 6B, camera 10e may include a number of arrays 100, 102, ..., formed of tubular collimator elements 104 which diverge toward the Z axis or axis of rotation 20e when viewed in a plane normal to the axis of rotation 20e.

Figure 7A:
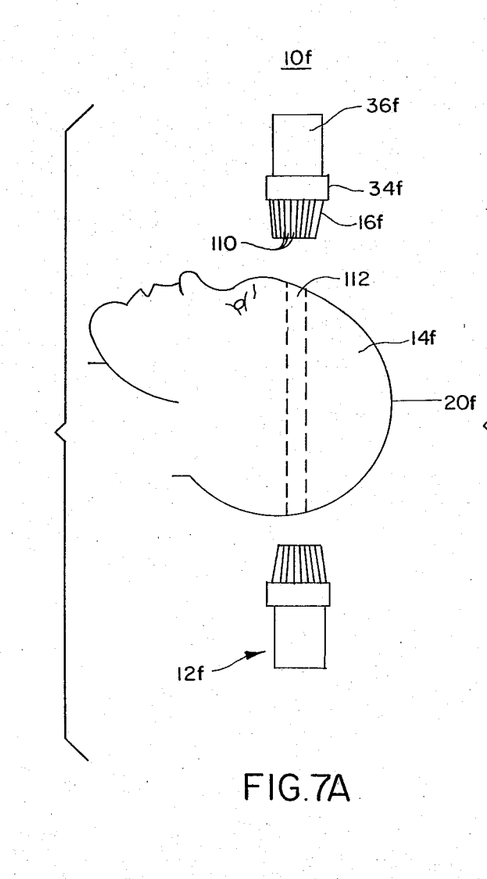
FIG. 7A is a side view of a camera according to this invention viewed in a plane through the axis of rotation for viewing narrow slices of an object with converging collimator elements.
Figure 7B:
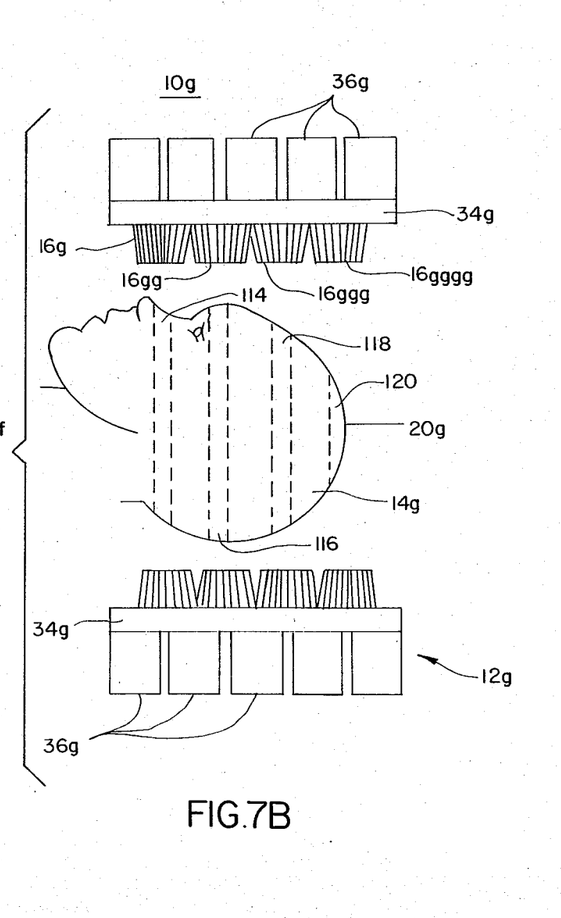
FIG. 7B is a view similar to FIG. 7A with a plurality of collimator elements for viewing a plurality of narrow slices.

The tubular collimator elements may also be nonparallel in a plane containing the axis of rotation 20f, FIG. 7A, where collimator 16f is shown with its tubular collimating elements 110 converging toward the rotational axis 20f in a plane containing rotational axis 20f in order to obtain a very narrow slice view 112 rather than the broader two-dimensional view such as obtainable with the apparatus in FIGS. 1–3. A number of such slices 114, 116, 118, 120 may be obtained by grouping a series of such collimators 16g, 16gg, 16ggg, 16gggg, FIG. 7B.

Figure 8:
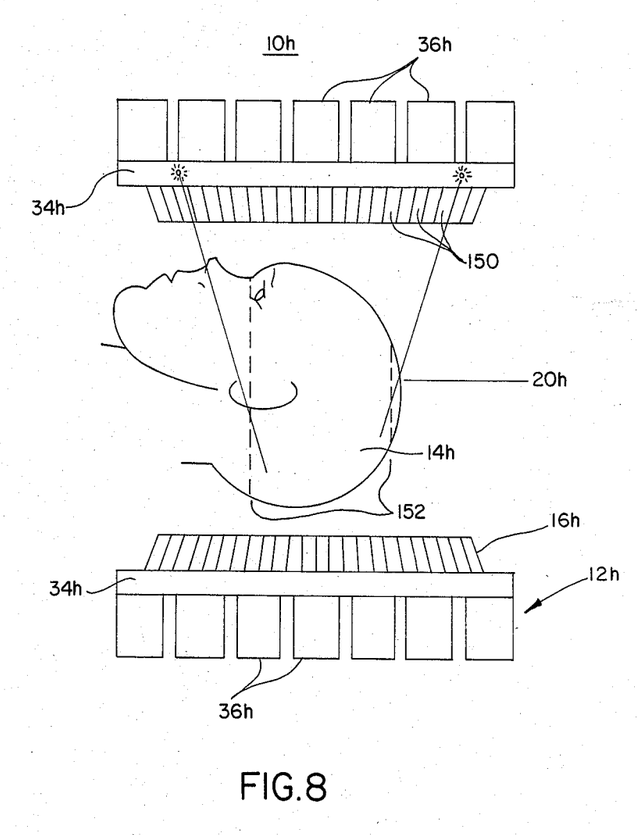
FIG. 8 is a side sectional view of a camera similar to that shown in FIGS. 1–3 with the collimator elements converging toward the rotational axis viewed in a plane containing the rotational axis.

In order to achieve high sensitivity by making maximum efficient use of the area of the scintillation crystal, collimators which have a large dimension along the Z axis, compared to the source field-of-view, may be provided with collimator elements 150, FIG. 8, designed to converge toward the axis of rotation 20h when viewed in the plane containing that axis. This is particularly useful for the three-dimensional reconstruction of source distributions of limited dimensions, such as a section of a patient's head 152 as shown in FIG. 8.

Other embodiments will occur to those skilled in the art and are within the following claims:

What is claimed is:

1. A radionuclide emission tomography camera for sensing gamma ray emissions from a source within the field of view, comprising:

a fixed, position-sensitive detector means, responsive to said gamma ray emissions and surrounding said field of view, for detecting the contact position and the trajectory from which a gamma ray emission originates, said fixed, position-sensitive detector including a single continuous stationary scintillation crystal;

rotatable collimator means, disposed between the fixed, position-sensitive detecto means and said field of view, and incuding at least one array of collimator elements, for restricting and collimating the gamma ray emissions; and means for rotating said collimator means relative to the fixed, position-sensitive detector, for exposing different sections of the position-sensitive detector to the gamma ray emissions in order to view the source from different angles.

2. A radionuclide emission tomography camera for sensing gamma ray emissions from a source within the field of view, comprising:

a fixed scintillation means surrounding the field of view for producing scintillations in response to incident gamma rays, said scintillation means including a single continuous stationary scintillation crystal;

photosensor means, responsive to said scintillation means, for producing an output in response to said scintillations;

rotatable collimator means contained within said scintillation means between said scintillation means and the field of view and including at least one array of collimator elements; and means for rotating said collimator means relative to the fixed scintillation means to provide a number of exposures of the gamma ray source in the field of view through each said array of collimator elements.

* * * * *